(12) United States Patent
Kang et al.

(10) Patent No.: US 9,694,043 B2
(45) Date of Patent: Jul. 4, 2017

(54) COMPOSITION FOR PREVENTING OR TREATING HEARING LOSS

(71) Applicant: UNIVERSITY-INDUSTRY COOPERATION GROUP OF KYUNG HEE UNIVERSITY, Yongin-si, Gyeonggi-do (KR)

(72) Inventors: Tong Ho Kang, Seoul (KR); Bin Na Hong, Seongnam-si (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 0 days.

(21) Appl. No.: 14/925,265

(22) Filed: Oct. 28, 2015

(65) Prior Publication Data

US 2016/0045558 A1    Feb. 18, 2016

Related U.S. Application Data

(63) Continuation of application No. 14/002,763, filed as application No. PCT/KR2012/001711 on Mar. 8, 2012, now abandoned.

(30) Foreign Application Priority Data

Mar. 10, 2011 (KR) ........................ 10-2011-0021389

(51) Int. Cl.
| | |
|---|---|
| A61K 36/39 | (2006.01) |
| A61K 36/64 | (2006.01) |
| A61K 36/804 | (2006.01) |
| A61K 36/43 | (2006.01) |
| A61K 36/185 | (2006.01) |
| A61K 9/00 | (2006.01) |
| A61K 9/14 | (2006.01) |
| A61K 9/20 | (2006.01) |
| A23L 33/105 | (2016.01) |
| A61K 9/08 | (2006.01) |

(52) U.S. Cl.
CPC ............ *A61K 36/39* (2013.01); *A23L 33/105* (2016.08); *A61K 9/0019* (2013.01); *A61K 9/145* (2013.01); *A61K 9/2018* (2013.01); *A61K 36/185* (2013.01); *A61K 36/43* (2013.01); *A61K 36/64* (2013.01); *A61K 36/804* (2013.01); *A23V 2002/00* (2013.01); *A61K 9/08* (2013.01); *A61K 9/2059* (2013.01)

(58) Field of Classification Search
CPC .............................. A61K 36/39; A61K 36/63
USPC ........................................................ 424/725
See application file for complete search history.

(56) References Cited

U.S. PATENT DOCUMENTS

| | | |
|---|---|---|
| 5,466,452 A | 11/1995 | Whittle |
| 6,790,464 B2 | 9/2004 | Kuok et al. |
| 7,223,424 B2 | 5/2007 | Chou |
| 2005/0058730 A1 | 3/2005 | Wan et al. |
| 2009/0232749 A1 | 9/2009 | Adler |
| 2009/0246186 A1 | 10/2009 | Shinagawa et al. |
| 2011/0052731 A1* | 3/2011 | Park .................... A61K 36/185 424/728 |
| 2013/0302310 A1 | 11/2013 | Sun et al. |

FOREIGN PATENT DOCUMENTS

| | | |
|---|---|---|
| JP | 63-284110 A | 11/1988 |
| JP | 2011-37738 A | 2/2011 |
| KR | 2001-067675 A | 7/2001 |
| KR | 10-2002-0074285 A | 9/2002 |
| KR | 2002-0085401 A | 11/2002 |
| KR | 2003-043326 A | 6/2003 |
| KR | 2006-033345 A | 4/2006 |
| KR | 811395 B1 | 3/2008 |
| KR | 101178025 B1 | 8/2012 |

OTHER PUBLICATIONS

Written Opinion Report for PCT/KR2012/001711 (translated). 2012 4 pages.*
Alton Meister, "Glutathione Deficiency Produced by Inhibition of its Synthesis, and its Reversal; Applications in Research and Therapy," Pharm. Ther., 1991, vol. 51, pp. 155-194.
Attias et al., "Oral Magnesium Intake Reduces Permanent Hearing Loss Induced by Noise Exposure," American Journal of Otolaryngology, 1994, vol. 15, No. 1, pp. 26-32.
Chun et al., "Two Cases of Sudden Deagness Treated with Herbal Accupuncture Therapy," The Journal of Oriental Medical Opthamology & Otolaryngology, 2003, vol. 16, No. 1, pp. 206-213.
Deepak Prasher, "New Strategies for Prevention and Treatment of Noise-Induced Hearing Loss," Lancet, 1998, vol. 352, pp. 1240-1242.
Ha et al., "A Clinical Study of Sudden Sensorineural Hearing Loss," The Journal of Oriental Medical Opthamology & Otolaryngology & Dermatology, 2003, vol. 16, No. 1, pp. 141-153.
Kopke et al., "Reduction of Noise-Induced Hearing Loss Using L-NAC and Salicylate in the Chinchilla," Hearing Research, 2000, vol. 149, 00. 138-146.
Kramer et al., "Efficacy of the Antioxidant N-acetylcysteine (NAC) in Protecting Ears Exposed to Loud Music," J. Am. Acad. Audiol., 2006, vol. 17, pp. 265-278.
Yamasoba et al., "Ebselen Prevents Noise-Induced Excitotoxicity and Temporary Threshold Shift," Neuroscience Letters, 2005, vol. 380, pp. 234-238.
Yu et al., "Protective Effect of Rehmannia glutinosa on the Cisplatin-Induced Damage of HEI-OC1 Auditory Cells Through Scavenging Free Radicals," Journal of Ethnopharmacology, 2006, vol. 107, pp. 383-388.
Website document entitled "Cuscuta L". Downloaded from web on Feb. 7, 2015. 3-pages. Obtained from website http:keys.lucidcentral.org/keys/FNW/FNW%20seeds/html/fact%20shettes/Cuscuta.htm.

* cited by examiner

*Primary Examiner* — Chris R Tate
(74) *Attorney, Agent, or Firm* — Sughrue Mion, PLLC

(57) ABSTRACT

A composition including *Cuscuta japonica* Choisy extract, or the extract of *Rehmannia glutinosa* Libschitz var. *purpurea MAKINO* and *Cuscuta japonica* Choisy is provided. The composition, which can be a pharmaceutical or food composition, is useful for preventing, ameliorating, or treating hearing loss. A method for ameliorating, preventing, or treating hearing loss, in particular, acoustic trauma, temporary or permanent hearing loss by effectively inhibiting the threshold shift induced by noise and the likes is disclosed.

13 Claims, 6 Drawing Sheets

COMPOSITION FOR PREVENTING OR TREATING HEARING LOSS

CROSS-REFERENCE TO RELATED APPLICATIONS

This is a Continuation of U.S. application Ser. No. 14/002,763 filed Sep. 3, 2013, which is a National Stage Entry of PCT International Application No. PCT/KR2012/001711 filed Mar. 8, 2012, which claims benefit of Korean Patent Application No. 10-2011-0021389 filed Mar. 10, 2011 of which disclosures are incorporated herein by reference in their entirety.

FIELD OF THE INVENTION

The present invention relates to a composition for preventing or treating hearing loss, comprising *Cuscuta japonica Choisy* extract or the extract of *Rehmannia glutinosa Libschitz* var. *purpurea MAKINO* and *Cuscuta japonica Choisy*.

BACKGROUND OF THE INVENTION

Ear can be classified into external ear from auricle to external auditory canal, middle ear with ear drum and auditory ossicle, and internal ear with cochlear canal and auditory nerve. Since sound is acoustic energy, it can be transmitted from auricle through external auditory canal to vibrate ear drum. The vibration of ear drum is transmitted to auditory ossicle comprised of 3 small bones connected to ear drum via mechanical energy. Strapes, the distal bone of auditory ossicle is connected to cochlear canal thereby transmitting the energy to lymph in cochlear canal. Transmitted energy can induce wave in lymph by which hair cells inside of cochlear canal can be stimulated. The movement of hair cells cause ionic change thereby neurotransmitters are transferred to the auditory nerve attached to hair cells in which acoustic sound is transmitted to brain in the form of electric energy. Sound transmitting organs such as external ear and middle ear can be recovered from diseases such as inflammation by treatment or surgery in most cases, and the hearing loss therefrom can be improved after treatment as well. Such hearing loss is called conductive hearing loss. Meanwhile, hearing loss caused by cochlear canal, the organ sensing sound, auditory nerve transmitting sound via electric energy, and the brain area participating in comprehensive roles such as distinction and understanding of sound is called sensorineural hearing loss.

Among sensory organs of body, auditory organ is one of the most basic and important sense for communication enabling to learn language, acquire knowledge, take part in social activities, and enjoy human life. Since most cases of hearing loss correspond to sensorineural hearing loss without current therapeutic methods available except prevention, once occurred, utilization of assistant means such as hearing aid or implantation of mechanical devices in the body are adopted to help hearing. Sensorineural hearing loss can be classified by the origin or time of outbreak, for example, innate hearing loss and acquired hearing loss depending on the time thereof. Innate hearing loss corresponds to the damage caused before birth from genetic, fetal or embryonic problems. Most cases of innate hearing loss are extremely severe in degree and impossible to learn language without separate training or education. In most cases of innate hearing loss, hearing aid or cochlear implant (the device to stimulate auditory nerve by electric stimulus to be implanted in the body and separate external device to be worn to listen) with high output is adopted to help hearing. However, if the degree of hearing loss is severe, the effectiveness of assistant devices such as hearing aid or cochlear implant is low with huge difference from normal hearing ability, thereby lots of inconvenience in daily lives remains. In case of acquired hearing loss, it can be caused by diseases, noise, drugs or accidents after birth, with causative agents such as noise, drugs, aging, trauma, and viruses. Among these, hearing loss caused by noise and aging is appreciably increasing recently. Development of science and technology results to the extension of life span, which in turn leads to the worldwide increase of elderly population rapidly. Since most cases of senile hearing loss also correspond to sensorineural hearing loss, there is no available drug or treatment method for treating or ameliorating disease except prevention or management thereof. Recent industrialization of society also contributes to rapid increase of the population suffered from hearing loss due to noise. Not only noise-induced hearing loss related with jobs such as workers or soldiers working in noisy environment but also that related with culture and leisure activities are increasing. According to the Korean Industrial Accidents Act, exposure to environmental noise of not less than 90 dB can cause damage to auditory sense. According to Occupational Safety and Health Administration (OSHA) of U.S., noise management is under control to the environment having noise level not less than 85 dB. From studies, human auditory organ was reported to be affected by noise not less than 75 dB. Considering that the noise level not less than 75 dB corresponds to that of roadside with driving cars, everyone in the industrial society can be regarded as living under the noise harmful to auditory organs. Besides of environment noise compelled, there are many cases of teenagers' exposure to loud sound such as leisure activity using MP3. Therefore, recent noise-induced hearing loss is seen in various age groups. Noise-induced hearing loss due to MP3 utilization and the likes from young age can damage hearing so that conversation can be held only with the help of hearing aid in their 40's. The degree of hearing loss gets more severe when accompanied with physical aging. As the degree of hearing loss gets severe, the effectiveness of assistant devices such as hearing aid is lowered. High degree of hearing loss will finally cause serious problems in communication. That is, the young generation experiencing current noise-induced hearing loss will suffer more severe hearing loss in their elderly. Hearing loss plays important roles in determining the quality of lives of various generations from the old to the young.

In these days, pre-clinical studies with antioxidants, N-methyl-D-aspartate (NMDA) antagonists, inhibitors of apoptosis, growth factors and the likes had been reported to discover effective substances for preventing and treating hearing loss, but they showed limitation to be progressed to the stage of clinical studies (Prasher D., *Lancet*, 352, pp 1240-1242, 1998). From initial study stage, the use of antioxidant to neutralize reactive oxygen species (ROS) and reactive nitrogen species (RNS) was proven to inhibit the cell damage of cochlear from animal experiments, but said substance was not developed into drugs. N-acetyl cysteine (NAC) and methionine (MET) were reported to be useful for preventing hearing loss, and NAC, the prodrug of GSH was shown to enhance the production of GSH (Meister A., *Pharmacol. Ther.*, 51, pp 155-194, 1991). High level of NAC showed preventive effects on noise-induced hearing loss with muco-polycarbohydrate-hydrolases for respiratory diseases wherein MET was converted into natural amino acid cysteine. Other investigators focused to inhibit apoptosis, and it was reported that GPx mimic played preventive roles in the damage of outer hair cells caused by noise. Among these studies, Mg, NAC and Ebselen showed their efficacy upto clinical stages. When 300 young soldiers were administered with 4 g of granular Mg daily and compared with control group administered with placebo at 1 week after exposure to noise, they were reported to have less degree of permanent hearing loss (Attias J. et al., *Am. J. Otolaryngol.*, 15, pp 26-32, 1994). Administration of Mg to the soldiers exposed to lower degree of noise showed decrease in temporary hearing loss, and 600 U.S. navy soldiers administered with NAC for 2 weeks during weapons training showed decrease in permanent hearing loss. From experiments with animal model, it was reported that high level of NAC had preventive effects on noise-induced hearing loss but limited effects on permanent hearing loss (Kopke R. D. et al., *Hear. Res.*, 149, pp 138-146, 2000; Kramer S. et al., *American Academy of Audiology Annual Convention and Expo, Washington D.C., USA*, Poster Presentation, pp 502, 2005). When 60 U.S. soldiers were taken Ebselen for 2 weeks during weapons training, it was reported to have effects on both temporary and permanent hearing losses (Yamasoba T. et al., *Neurosci. Lett.*, 380, pp 234-238, 2005).

Until now, there is no approved drug for preventing and treating noise-induced hearing loss, with only academic report of preclinical studies and Mg, NAC and Ebselen drug in clinical stages.

Meanwhile, in the field of oriental medicine, it was reported that steamed *Rehmannia glutinosa Libschitz* var. *purpurea MAKINO* had been used in the past for inner ear diseases such as ear noise and hearing loss, and ethanol extract of steamed *Rehmannia glutinosa Libschitz* var. *purpurea MAKINO* inhibited lipid peroxidation and removed the activities of free radical to protect HEI-OC1 auditory cells from cisplatin-induced damage (Hyeon-Hee Yu et al., *Journal of Ethnopharmacology*, Volume 107, Issue 3, pp 383-388, 2006).

Under the circumstances, the present inventors searched various active substances among natural substances with high safety to prevent or treat hearing loss. Surprisingly, it was found that *Cuscuta japonica Choisy* extract inhibited the shift of hearing threshold induced by noise effectively, and further the extract of *Rehmannia glutinosa Libschitz* var. *purpurea MAKINO* and *Cuscuta japonica Choisy* showed superior effects than individual extracts, thereby completing the present invention.

DESCRIPTION OF THE INVENTION

Technical Subjects

It is the purpose of the present invention to provide a pharmaceutical composition for preventing or treating hearing loss.

In addition, it is the purpose of the present invention to provide a food composition for preventing or treating hearing loss.

Technical Solutions

The present invention provides a pharmaceutical composition for preventing or treating hearing loss, comprising *Cuscuta japonica Choisy* extract.

The present invention provides a pharmaceutical composition for preventing or treating hearing loss, comprising the extract of *Rehmannia glutinosa Libschitz* var. *purpurea MAKINO* and *Cuscuta japonica Choisy*.

The present invention provides a food composition for preventing or ameliorating hearing loss, comprising *Cuscuta japonica Choisy* extract.

The present invention provides a food composition for preventing or ameliorating hearing loss, comprising the extract of *Rehmannia glutinosa Libschitz* var. *purpurea MAKINO* and *Cuscuta japonica Choisy*.

The composition of the invention can be preferably adopted to the prevention or treatment of hearing loss induced by various causes, in particular noise-induced hearing loss.

Said *Cuscuta japonica Choisy* extract can be obtained by extract process comprising the extraction step of *Cuscuta japonica Choisy* with the extraction solvent selected from the group consisting of water, $C_1$~$C_4$ alcohol, and the mixed solvent of water and $C_1$~$C_4$ alcohol, preferably with aqueous ethanol.

Said extract of *Rehmannia glutinosa Libschitz* var. *purpurea MAKINO* and *Cuscuta japonica Choisy* can be obtained by extract process comprising the extraction step of *Rehmannia glutinosa Libschitz* var. *purpurea MAKINO* and *Cuscuta japonica Choisy* respectively with the extraction solvent selected from the group consisting of water, $C_1$~$C_4$ alcohol, and the mixed solvent of water and $C_1$~$C_4$ alcohol, preferably with aqueous ethanol, and then the mixing step of respective extracts, or the extraction step of *Rehmannia glutinosa Libschitz* var. *purpurea MAKINO* and *Cuscuta japonica Choisy* together with the above mentioned extraction solvent.

Said *Rehmannia glutinosa Libschitz* var. *purpurea MAKINO* can be at least one selected from the group consisting of raw *Rehmannia glutinosa Libschitz* var. *purpurea MAKINO*, dried *Rehmannia glutinosa Libschitz* var. *purpurea MAKINO* and steamed *Rehmannia glutinosa Libschitz* var. *purpurea MAKINO*, and said *Cuscuta japonica Choisy* can be at least one selected from the group consisting of *Cuscuta chinensis Lam.*, *Cuscuta pentagona Engelm.*, *Cuscuta japonica Choisy*, and *Cuscuta australis R. Br.*

Advantageous Effects

The composition according to the present invention can effectively inhibit the shift of hearing threshold induced by noise and the likes thereby inhibiting hearing loss, in particular, acoustic trauma, temporary or permanent noise-induced hearing loss. Therefore, the composition according to the present invention is useful for preventing or treating hearing loss. In addition, it can be administered orally, thereby drug compliance of patients can be enhanced.

BEST MODES FOR PRACTICING THE INVENTION

Figure 1:
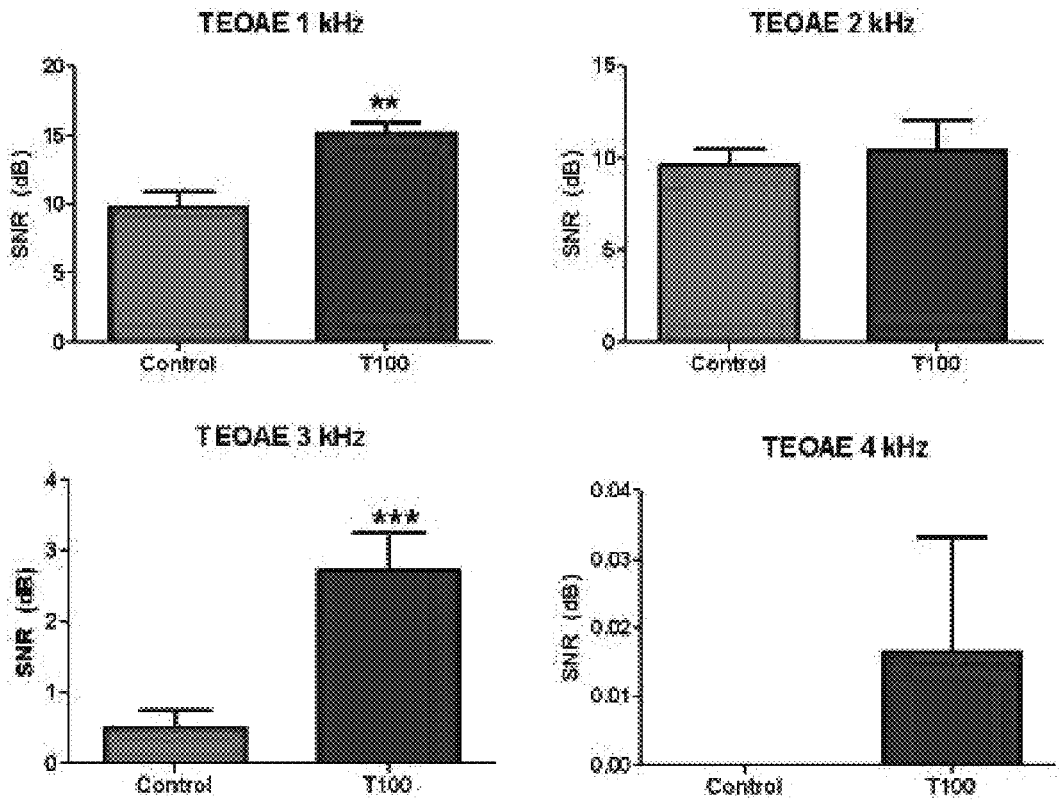
FIG. 1 shows the measurement of *Cuscuta japonica Choisy* extract in transient evoked otoacoustic emission (TEOAE) test after exposure to noise (control: not treated group, T100: test group treated with *Cuscuta japonica Choisy* extract).

The term "hearing loss" used in this specification comprises conductive hearing loss and sensorineural hearing loss. Preferably, it comprises conductive hearing loss induced by various causes such as noise, drugs, aging, trauma, and viruses. In particular, sensorineural hearing loss comprises noise induced hearing loss (NIHL) representing symptoms of damage in cochlear canal and auditory nerve due to various noises. Said noise-induced hearing loss comprises acoustic trauma hearing loss, temporary threshold shift (TTS) due to short-term noise and permanent threshold shift (PTS) due to long-term noise.

The present invention provides a pharmaceutical composition for preventing or treating hearing loss, comprising *Cuscuta japonica Choisy* extract.

Further, the present invention provides a pharmaceutical composition for preventing or treating hearing loss, comprising the extract of *Rehmannia glutinosa Libschitz* var. *purpurea MAKINO* and *Cuscuta japonica Choisy*.

*Cuscuta japonica Choisy* of the invention is the seed in egg-shaped fruit of annular plant *Cuscuta japonica Choisy* (name of herb medicine: *Cuscuta japonica Choisy*) belonging to Convolvulaceae, and can be at least one selected from the group consisting of *Cuscuta chinensis Lam.*, *Cuscuta pentagona Engelm.*, *Cuscuta japonica Choisy*, and *Cuscuta australis R. Br. Rehmannia glutinosa Libschitz* var. *purpurea MAKINO* of the invention can be at least one selected from the group consisting of raw *Rehmannia glutinosa Libschitz* var. *purpurea MAKINO*, dried *Rehmannia glutinosa Libschitz* var. *purpurea MAKINO* and steamed *Rehmannia glutinosa Libschitz* var. *purpurea MAKINO*, of which steamed *Rehmannia glutinosa Libschitz* var. *purpurea MAKINO* is preferably used. Steamed *Rehmannia glutinosa Libschitz* var. *purpurea MAKINO* represents the product obtained by steaming and drying raw *Rehmannia glutinosa Libschitz* var. *purpurea MAKINO* nine times, whereas raw *Rehmannia glutinosa Libschitz* var. *purpurea MAKINO* represents the root peeled with cuticular layer of perennial plant *Rehmannia glutinosa Libschitz* var. *purpurea MAKINO* (name of herb medicine: *Rehmannia glutinosa Libschitz* var. *purpurea MAKINO*) belonging to Scrophulariaceae, and dried *Rehmannia glutinosa Libschitz* var. *purpurea MAKINO* represents the product prepared by drying *Rehmannia glutinosa Libschitz* var. *purpurea MAKINO*.

The extract of *Rehmannia glutinosa Libschitz* var. *purpurea MAKINO* and *Cuscuta japonica Choisy* represents not only the extract prepared by extracting *Rehmannia glutinosa Libschitz* var. *purpurea MAKINO* and *Cuscuta japonica Choisy* together (mixed extract of *Rehmannia glutinosa Libschitz* var. *purpurea MAKINO* and *Cuscuta japonica Choisy*) but also the mixture of extracts prepared by extracting them respectively (the mixture of *Rehmannia glutinosa Libschitz* var. *purpurea MAKINO* extract and *Cuscuta japonica Choisy* extract).

The extract of *Rehmannia glutinosa Libschitz* var. *purpurea MAKINO* and *Cuscuta japonica Choisy* of the invention comprises about 1:1.8 to about 1:9 ratio of *Rehmannia* glutinosa Libschitz var. purpurea MAKINO to Cuscuta japonica Choisy. The extract of Rehmannia glutinosa Libschitz var. purpurea MAKINO and Cuscuta japonica Choisy blended within the abovementioned ratio can present preferable preventive or therapeutic effects on hearing loss.

Said Cuscuta japonica Choisy extract or the extract of Rehmannia glutinosa Libschitz var. purpurea MAKINO and Cuscuta japonica Choisy can be obtained by extract process comprising the extraction step of Cuscuta japonica Choisy, or Rehmannia glutinosa Libschitz var. purpurea MAKINO and Cuscuta japonica Choisy with the extraction solvent (first extraction solvent) selected from the group consisting of water, $C_1$~$C_4$ alcohol, and the mixed solvent of water and $C_1$~$C_4$ alcohol. Said first extraction solvent is preferably aqueous ethanol. The extract of Rehmannia glutinosa Libschitz var. purpurea MAKINO and Cuscuta japonica Choisy can be also obtained by extracting Rehmannia glutinosa Libschitz var. purpurea MAKINO and Cuscuta japonica Choisy respectively as above, obtaining Rehmannia glutinosa Libschitz var. purpurea MAKINO extract and Cuscuta japonica Choisy extract, and then mixing them.

Said extraction process can be performed with about 1 to 20 w/w, and preferably about 3 to 10 w/w of said first extraction solvent, preferably the mixed solvent of water and ethanol based on the weight of Cuscuta japonica Choisy, or Rehmannia glutinosa Libschitz var. purpurea MAKINO and Cuscuta japonica Choisy. As for said mixed solvent, about 70% aqueous ethanol can be preferably used. Extraction can be conducted by extracting methods known in the art, including but not limited to maceration, extraction with hot water, ultrasonic extraction, and reflux extraction. The person in the art can employ various extraction temperature appropriate to the extraction method selected, for example, including but not limited to from 20 to 100° C. Further, extraction time can vary depending on the extraction method and can be appropriately selected by the person in the art, for example, including the range of about 1 hour to 10 days for single or multiple times, but not limited thereto. Preferably, said extraction can be performed 2 or 3 times with said first extraction solvent at room temperature for about 2 days. The extract obtained by extraction with said first extraction solvent can be filtered by conventional method to give liquid form wherein impurities are removed, or the extract in liquid form can be further concentrated under reduced pressure and/or dried to give powder form.

In addition, said extraction process can optionally further comprise the selection stage to obtain the fraction with high proportion of active ingredient. That is, the extract obtained by extraction with said first solvent is dispersed in water, and then is extracted with second extraction solvent, such as water-saturated $C_4$ alcohol to raise the proportion of active ingredient in the resulting extract.

The pharmaceutical composition of the invention can comprise 1 to 80 weight % of Cuscuta japonica Choisy extract or the extract of Rehmannia glutinosa Libschitz var. purpurea MAKINO and Cuscuta japonica Choisy based on the total weight of the composition.

The pharmaceutical composition of the invention can comprise pharmaceutically acceptable carriers, and can be formulated into the form of oral preparation such as powder, granule, tablet, capsule, suspension, emulsion, syrup, and aerosol, and external preparation, suppository preparation and sterile injection according to the conventional methods therefor.

As for said pharmaceutically acceptable carriers, it can comprise conventionally used carriers in the art, including but not limited to lactose, dextrose, sucrose, sorbitol, Mannitol, xylitol, erythritol, maltitol, starch, acacia gum, alginate, gelatin, calcium phosphate, calcium silicate, cellulose, methyl cellulose, microcrystalline cellulose, polyvinyl pyrollidone, water, methylhydroxybenzoate, propylhydroxybenzoate, talc, magnesium stearate and mineral oils. Further, the pharmaceutical composition of the invention comprises diluents, excipients and other pharmaceutically acceptable additives such as fillers, expanders, binders, humectants, disintegrants, and surfactants.

When the pharmaceutical composition of the invention is formulated into oral solid preparation, it comprises tablet, pillet, powder, granule, capsule and the likes, wherein such solid preparation can comprise but not limited to at least one excipient, such as starch, calcium carbonate, sucrose or lactose, and gelatin, and lubricant, such as magnesium stearate, and talc.

When the pharmaceutical composition of the invention is formulated into oral liquid preparation, it comprises suspension, drink, emulsion and syrup, wherein such preparation can comprise but not limited to diluent such as water, and liquid paraffin, humectant, sweetening agent, odorant and preservative.

When the pharmaceutical composition of the invention is formulated into parental preparation, it comprises sterile solution, non-aqueous solution, suspension, emulsion, lyophilized preparation and suppository, wherein such preparation can comprise but not limited to non-aqueous solvent or suspending agent such as propylene glycol, polyethylene glycol, vegetable oil like olive oil and injectable esters like ethylolate. The base for suppository can comprise but not limited to witepsol, macrogol, Tween 61, cacao butter, laurine butter, and glycerogeletain.

The dosage of Cuscuta japonica Choisy extract or the extract of Rehmannia glutinosa Libschitz var. purpurea MAKINO and Cuscuta japonica Choisy to be contained in the pharmaceutical composition of the invention can vary depending on the status, weight and age of patient, severity of disease, formulation, administration route and period, but it can be properly selected by the person in the art. For example, said Cuscuta japonica Choisy extract or the extract of Rehmannia glutinosa Libschitz var. purpurea MAKINO and Cuscuta japonica Choisy can be administered with dosage of 1 to 2000 mg/kg/day, and preferably 10 to 2000 mg/kg/day, which can be given once a day or divided into several times a day.

The pharmaceutical composition of the invention can be given by various routes, for example oral, intraperitoneal or intravenous, intramuscular, subcutaneous, intrauterine, intrathecal or intracerebroventricular injection to mammal including rat, mouse, livestock, and human.

The pharmaceutical composition of the invention is effective in preventing or treating hearing loss including conductive hearing loss and sensorineural hearing loss, and particularly effective in preventing or treating noise-induced hearing loss including acoustic trauma hearing loss, temporary threshold shift due to short-term noise and permanent threshold shift due to long-term noise.

In addition, the present invention comprises the food composition for preventing or ameliorating hearing loss, preferably noise-induced hearing loss, which comprising Cuscuta japonica Choisy extract or the extract of Rehmannia glutinosa Libschitz var. purpurea MAKINO and Cuscuta japonica Choisy.

The food composition of the invention can be used as health functional food. Said "health functional food" means the food manufactured and processed by using materials and substance with useful functionality for human body in accordance with the Health Functional Food Act No. 6727, wherein "functionality" means that it is taken for the purpose of obtaining useful health use such as controlling nutrients or influencing physiology for body structure and function.

The food composition of the invention can comprise conventional food additives, and the acceptability of said "food additives" shall be judged by specifications and standards for relevant items in accordance with general principles and test methods of Korean Food Additives Codex, unless there is no other regulation thereto.

Items listed in said "Korean Food Additives Codex" include, for example, chemically synthesized additives such as ketones, glycine, potassium citrate, nicotinic acid, and cinnamic acid, natural additives such as persimmon color, licorice extract, crystalline cellulose, kaoliang color, and guar gum, and compound additives such as sodium L-glutamate, alkali additives for noodle, preservative additives, and tar color.

The food composition of the invention can comprise 0.01 to 95 weight %, preferably 1 to 80 weight % of *Cuscuta japonica Choisy* extract or the extract of *Rehmannia glutinosa Libschitz* var. *purpurea MAKINO* and *Cuscuta japonica Choisy* based on the total weight of composition, for the purpose of preventing and/or ameliorating hearing loss, particularly noise-induced hearing loss. *Cuscuta japonica Choisy* extract or the extract of *Rehmannia glutinosa Libschitz* var. *purpurea MAKINO* and *Cuscuta japonica Choisy* to be contained to the food composition of the invention can be obtained by the same method mentioned in the preparation of above pharmaceutical composition.

In addition, the food composition of the invention can be prepared and processed into the forms of tablet, capsule, powder, granule, liquid, pillet and the likes for the purpose of preventing and/or ameliorating hearing loss.

For example, said health functional food in tablet form can be prepared by granulating the mixture of *Cuscuta japonica Choisy* extract or the extract of *Rehmannia glutinosa Libschitz* var. *purpurea MAKINO* and *Cuscuta japonica Choisy*, and excipients, binders, disintegrants and other additives according to conventional method, then adding lubricants and the likes and compress-molding them, or directly compress-molding the said mixture. Further, said health functional food in tablet form can optionally comprise tasty acids and the likes, and can be optionally coated with appropriate coating agents.

Among health functional food in capsule form, hard capsule can be prepared by filling the mixture of *Cuscuta japonica Choisy* extract or the extract of *Rehmannia glutinosa Libschitz* var. *purpurea MAKINO* and *Cuscuta japonica Choisy*, and additives such as excipients, or granules thereof or coated granules thereof into conventional hard capsule, whereas soft capsule can be prepared by filling the mixture of steamed extract of *Rehmannia glutinosa Libschitz* var. *purpurea MAKINO* and *Cuscuta japonica Choisy*, and additives such as excipients into capsule base such as gelatin. Said soft capsule can optionally comprise plasticizers such as glycerin or sorbitol, coloring agents and preservatives.

The health functional food in the form of pillet can be formulated by compacting the mixture of *Cuscuta japonica Choisy* extract or the extract of *Rehmannia glutinosa Libschitz* var. *purpurea MAKINO* and *Cuscuta japonica Choisy*, and excipients, binders, disintegrants and the likes with appropriate method, and optionally coating with white sugar or other proper coating agents or glidant-coating with starch, talc or appropriate substances.

The health functional food in the form of granule can be prepared with the mixture of *Cuscuta japonica Choisy* extract or the extract of *Rehmannia glutinosa Libschitz* var. *purpurea MAKINO* and *Cuscuta japonica Choisy*, and excipients, binders, disintegrants and the likes by proper methods, and optionally comprise fragrance, tasty acids and the likes. When conducting particle size test with the health functional food in the form of granule with No. 12 (1680 μm), No. 14 (1410 μm) and No. 45 (350 μm) sieves, the residual amount through sieves can be none with No. 12 sieve, and not more than 5.0% with No. 14 sieve whereas the passing amount with No. 45 sieve can be not more than 15.0% based on the total amount thereof.

The definition of such terms as excipient, binder, disintegrant, lubricant, tasty acid, fragrance and the likes is described in literatures known in the art and encompasses that with same or similar functions (Korean Pharmacopoeia, Explanation, Moonsung Pub., Korea college of pharmacy conference, 5th Ed., p 33-48, 1989).

Hereinafter, the present invention will be further described in detail with examples and experiment examples. However, these example and experiment examples are to illustrate the invention, not to limit the scope of the invention thereto.

EXAMPLES

Example 1

Preparation of *Cuscuta japonica Choisy* Extract 500 g of *Cuscuta japonica Choisy* was added to 10 L of 70% ethanol and extracted in extraction vessel at 80° C. Supernatant was collected by repeating said procedure 3 times, concentrated with vacuum concentrator (EYELA, N-N) at 45° C., and then lyophilized with ILSHIN lyophilizer at the temperature of no more than −40° C. for at least 12 hours to obtain 149.8 g of *Cuscuta japonica Choisy* extract.

Example 2

Preparation of the Extract of *Rehmannia glutinosa Libschitz* Var. *Purpurea MAKINO* and *Cuscuta japonica Choisy*

500 g of the mixture comprising 25% of steamed *Rehmannia glutinosa Libschitz* var. *purpurea MAKINO* and 75% of *Cuscuta japonica Choisy* with regard to total volume was added to 10 L of 70% ethanol 10 l and extracted in extraction vessel at 80° C. Supernatant was collected by repeating said procedure 3 times, concentrated with vacuum concentrator (EYELA, N-N) at 45° C., and then lyophilized with ILSHIN lyophilizer at the temperature of no more than −40° C. for at least 12 hours to obtain 97.6 g of steamed extract of *Rehmannia glutinosa Libschitz* var. *purpurea MAKINO* and *Cuscuta japonica Choisy*.

Example 3

Preparation of *Rehmannia glutinosa Libschitz* Var. *Purpurea MAKINO* and *Cuscuta japonica Choisy* Fraction 50 g of the extract of *Rehmannia glutinosa Libschitz* var. *purpurea MAKINO* and *Cuscuta japonica Choisy* obtained from above Example 2 was suspended into 1 L of distilled water and dissolved by adding 1 L of water-saturated butanol, and then only the fraction soluble in water-saturated butanol layer was separated from funnel to vacuum dry. This procedure was repeated 5 times to obtain 9.8 g of fraction.

Comparative Example

Comparative Example 1

Preparation of Steamed *Rehmannia glutinosa Libschitz* Var. *purpurea* MAKINO Extract The same procedure described in example 1 was conducted except 500 g of steamed *Rehmannia glutinosa Libschitz* var. *purpurea* MAKINO was used instead of 500 g of *Cuscuta japonica Choisy* to obtain 104.0 g of steamed *Rehmannia glutinosa Libschitz* var. *purpurea* MAKINO extract.

Experiment Examples

Experiment example 1

Identification of Protective Effect on Hair Cells with *Cuscuta japonica Choisy* Extract after Exposure to Noise—Transient Evoked Otoacoustic Emission (TEOAE) Experiment In order to identify the effect on the damage of hair cells of cochlea with *Cuscuta japonica Choisy* extract after exposure to noise, transient evoked otoacoustic emission (TEOAE) experiment was conducted.

Transient evoked otoacoustic emission (TEOAE) experiment is to measure the sound developed in hair cells of cochlea from outside based on the fact that healthy hair cells develop sound as a response to acoustic stimulus. On the other hand, such response in damaged hair cells tends to diminish or disappear. Since noise-induced stimulus can cause serious damage on hair cells of cochlea, transient evoked otoacoustic emission (TEOAE) experiment was conducted to identify the effect on noise-induced hearing loss of *Cuscuta japonica Choisy* extract.

4 groups, each comprising 8 mice to be administered with 100 mg/kg of the *Cuscuta japonica Choisy* extract prepared in example 1 and 8 mice of (untreated) control group were divided and assessed. Wide range noise of 120 dB was exposed for 2 hours, *Cuscuta japonica Choisy* extract was fed at 24 hours after exposure to noise and orally administered at the same time of day. Transient evoked otoacoustic emission (TEOAE) was measured at the $14^{th}$ day after exposure to noise. For transient evoked otoacoustic emission (TEOAE) measurement, mouse was administered with Ketamine (4.57 mg/kg) and Silazine (0.43 mg/kg) to anesthetize, and tested while maintaining body temperature of 37±0.5° C. At the time of measuring transient evoked otoacoustic emission (TEOAE), stimulation tone was set to 90 dB with test frequency of 1, 2, 3, and 4 kHz.

As shown in FIG. 1, at 1 kHz TEOAE, *Cuscuta japonica Choisy* extract (T100) treated group showed significant higher TEOAE response than control group, while at 2 kHz, *Cuscuta japonica Choisy* extract (T100) treated group showed higher but not significant TEOAE response than control group. At 3 kHz TEOAE, *Cuscuta japonica Choisy* extract (T100) treated group showed significant higher TEOAE response than control group, and at 4 kHz TEOAE, *Cuscuta japonica Choisy* extract (T100) treated group showed significant higher TEOAE response than control group as well. Control group showed clear damage on hair cells demonstrated by low level of response, particularly at 3 and 4 kHz TEOAE, while *Cuscuta japonica Choisy* extract (T100) treated group showed less damage on hair cells at both frequency after exposure to noise.

Experiment Example 2

Identification of Ameliorating Effect on Hearing with *Cuscuta japonica Choisy* Extract after Exposure to Noise—By Using Click Stimulation Tone In order to identify the effect on the presence of hearing sense with *Cuscuta japonica Choisy* extract by measuring threshold after exposure to noise, hearing threshold experiment was conducted by using auditory brainstem response (ABR).

Auditory brainstem response (ABR) experiment is to test the response to sound by measuring the electric energy transmitted from auditory nerve by sound stimulus. Since the response obtained by sound from external ear through middle ear and cochlear canal to auditory nerve reflects the total condition of external ear, middle ear, and cochlear canal, it demonstrates actual auditory energy reaching to brain. Hearing threshold means the minimal point of hearing sense to hear, and normal mouse can show response with as small sound as 20 dB on average.

4 groups, each comprising 8 mice to be administered with 100 mg/kg of the *Cuscuta japonica Choisy* extract prepared in example 1 and 8 mice of untreated control group were divided and assessed. Pure sound noise of 120 dB at 4 kHz was exposed for 2 hours, *Cuscuta japonica Choisy* extract was fed for 24 hours after exposure to noise and orally administered at the same time of day. Hearing threshold was measured before and 1, 4 and 7 days after exposure to noise. To test auditory brainstem response (ABR), Ketamine (4.57 mg/kg) and Silazine (0.43 mg/kg) were intramuscularly injected to mouse to anesthetize while maintaining body temperature of 37±0.5° C. At the time of measuring auditory brainstem response (ABR), stimulation tone was given with click sound of wide range stimulation tone starting from 90 dB and decreased by 5 dB to find threshold, the minimal sound showing response.

Figure 2:
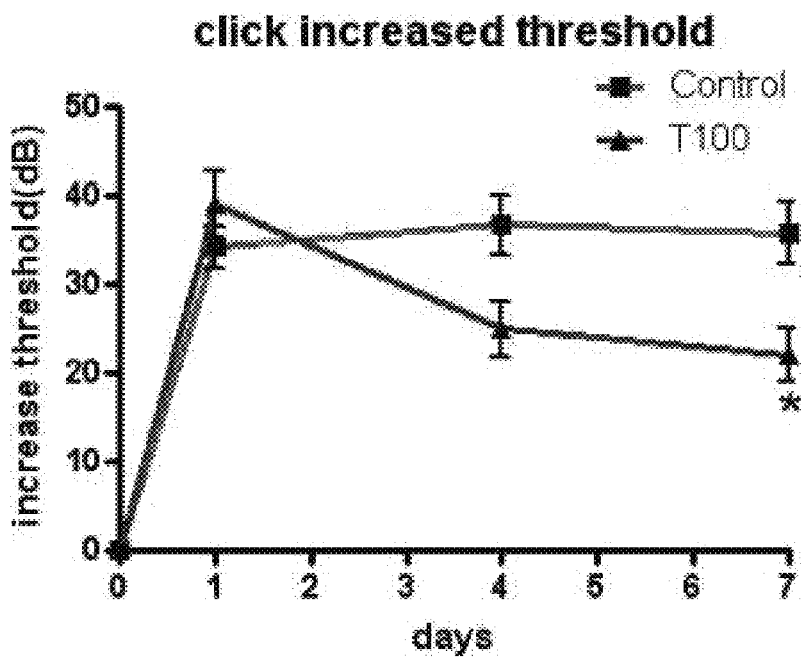
FIG. 2 shows the measurement of *Cuscuta japonica Choisy* extract in hearing threshold test by auditory brainstem response (ABR) with click stimulation tone after exposure to noise (control: not treated group, T100: test group treated with *Cuscuta japonica Choisy* extract).

As shown in FIG. 2, control group showed increased hearing threshold at 24 hours after exposure to noise and maintained similar threshold for 7 days which suggesting permanent hearing damage. Meanwhile, *Cuscuta japonica Choisy* extract (T100) treated group showed the decrease in threshold since 4 days after exposure to noise, and 17 dB decrease than before administration shown at 7 days after exposure identified significant ameliorating effects compared to control group. From high ameliorating effects on hearing threshold with *Cuscuta japonica Choisy* extract (T100) treated group, it can be verified that *Cuscuta japonica Choisy* extract (T100) is effective in preventing and treating noise-induced hearing loss.

Experiment Example 3

Identification of Ameliorating Effect on Hearing with *Cuscuta japonica Choisy* Extract after Exposure to Noise—By Using 3 kHz TB Stimulation Tone In order to identify the ameliorating effect of *Cuscuta japonica Choisy* extract by measuring hearing threshold at 3 kHz stimulation tone after exposure to noise, hearing threshold experiment was conducted by using auditory brainstem response (ABR).

Experiment was conducted as same as experiment example 2 except that stimulation tone was given at 3 kHz tone burst (TB) from 70 dB and decreased by 5 dB. The obtained result is shown at FIG. 3.

Figure 3:
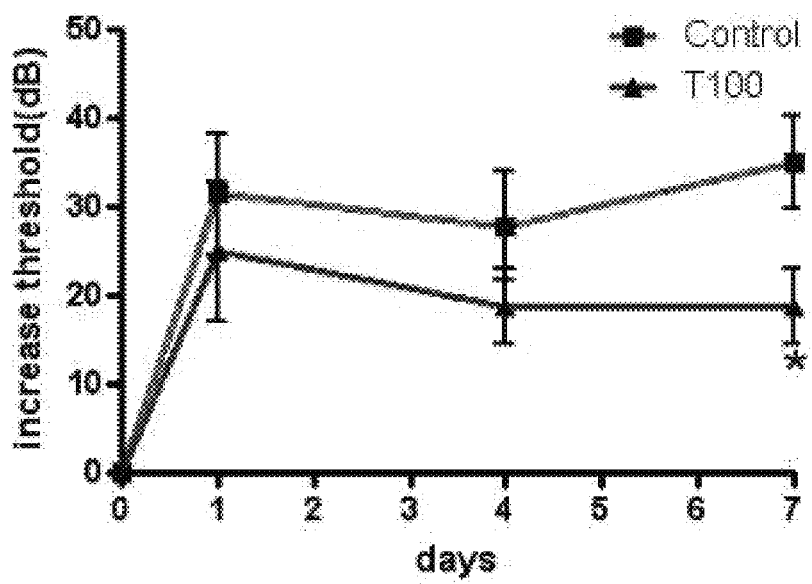
FIG. 3 shows the measurement of *Cuscuta japonica Choisy* extract in hearing threshold test by auditory brainstem response (ABR) with 3 kHz TB stimulation tone after exposure to noise (control: not treated group, T100: test group treated with *Cuscuta japonica Choisy* extract).

As shown in FIG. 3, control group showed increased hearing threshold at 24 hours after exposure to noise and maintained similar threshold for 7 days which suggesting permanent hearing damage. Meanwhile, *Cuscuta japonica Choisy* extract (T100) treated group showed the decrease in threshold since 4 days after exposure to noise, and 7 dB decrease than before administration shown at 7 days after exposure identified significant ameliorating effects compared to control group. As found in test result with click stimulation tone, high ameliorating effects on hearing threshold with *Cuscuta japonica Choisy* extract (T100) treated group was found to identify that *Cuscuta japonica Choisy* extract (T100) is effective in preventing and treating noise-induced hearing loss.

Experiment Example 4

Identification of Ameliorating Effect on Hearing with *Cuscuta japonica Choisy* Extract after Exposure to Noise—By Using 4 kHz TB Stimulation Tone In order to identify the ameliorating effect of *Cuscuta japonica Choisy* extract by measuring hearing threshold at 4 kHz stimulation tone after exposure to noise, hearing threshold experiment was conducted by using auditory brainstem response (ABR).

Experiment was conducted as same as experiment example 2 except that stimulation tone was given at 4 kHz tone burst (TB) which is the same stimulation tone used in noise exposure from 70 dB and decreased by 5 dB. The obtained result is shown at FIG. 4.

Figure 4:
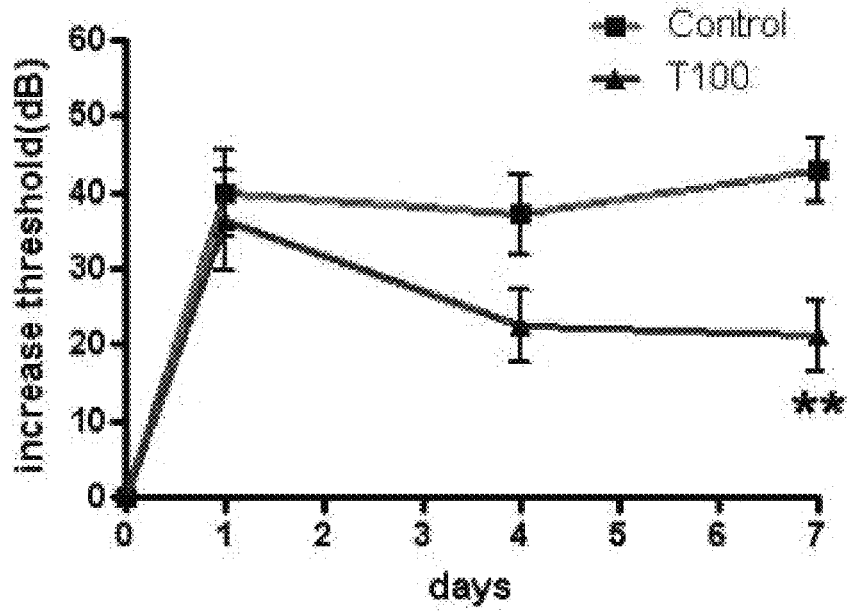
FIG. 4 shows the measurement of *Cuscuta japonica Choisy* extract in hearing threshold test by auditory brainstem response (ABR) with 4 kHz TB stimulation tone after exposure to noise (control: not treated group, T100: test group treated with *Cuscuta japonica Choisy* extract).

As shown in FIG. 4, control group showed increased hearing threshold at 24 hours after exposure to noise and maintained similar threshold for 7 days which suggesting permanent hearing damage. Meanwhile, *Cuscuta japonica Choisy* extract (T100) treated group showed the decrease in threshold since 4 days after exposure to noise, and 15 dB decrease than before administration shown at 7 days after exposure identified significant ameliorating effects compared to control group. As found in test result with click stimulation tone and 3 kHz TB stimulation tone, ameliorating effects on hearing threshold with *Cuscuta japonica Choisy* extract (T100) treated group was found to identify that *Cuscuta japonica Choisy* extract (T100) is effective in preventing and treating noise-induced hearing loss.

Experiment Example 5

Identification of Ameliorating Effect on Hearing with *Cuscuta japonica Choisy* Extract after Exposure to Noise—By Using 6 kHz TB Stimulation Tone In order to identify the ameliorating effect of *Cuscuta japonica Choisy* extract by measuring hearing threshold at 6 kHz stimulation tone after exposure to noise, hearing threshold experiment was conducted by using auditory brainstem response (ABR).

Experiment was conducted as same as experiment example 2 except that stimulation tone was given at 6 kHz tone burst (TB) which frequency is close to the stimulation tone used in noise exposure from 70 dB and decreased by 5 dB. The obtained result is shown at FIG. 5.

Figure 5:
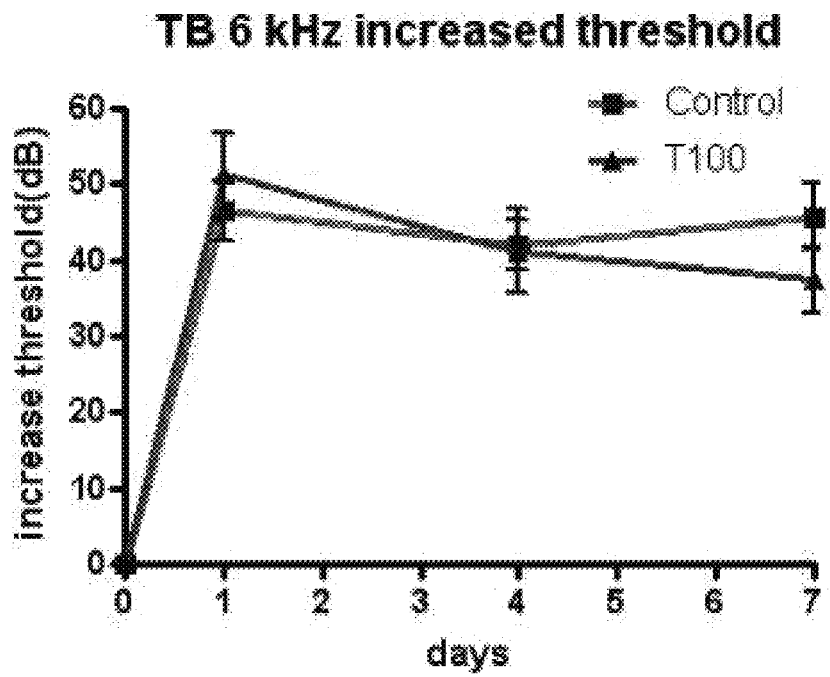
FIG. 5 shows the measurement of *Cuscuta japonica Choisy* extract in hearing threshold test by auditory brainstem response (ABR) with 6 kHz TB stimulation tone after exposure to noise (control: not treated group, T100: test group treated with *Cuscuta japonica Choisy* extract).

As shown in FIG. 5, control group showed increased hearing threshold at 24 hours after exposure to noise and maintained similar threshold for 7 days which suggesting permanent hearing damage. Meanwhile, *Cuscuta japonica Choisy* extract (T100) treated group showed the decrease in threshold since 4 days after exposure to noise, and 13 dB decrease than before administration shown at 7 days after exposure identified ameliorating effects compared to control group. As found in test results with click stimulation tone and 3 kHz and 4 kHz TB stimulation tone, ameliorating effects on hearing threshold with *Cuscuta japonica Choisy* extract (T100) treated group was found to identify that *Cuscuta japonica Choisy* extract (T100) is effective in preventing and treating noise-induced hearing loss.

Experiment Example 6

Identification of Ameliorating Effect on Hearing with *Cuscuta japonica Choisy* Extract after Exposure to Noise—By Using 8 kHz TB Stimulation Tone In order to identify the ameliorating effect of *Cuscuta japonica Choisy* extract by measuring hearing threshold at 8 kHz stimulation tone after exposure to noise, hearing threshold experiment was conducted by using auditory brainstem response (ABR).

Experiment was conducted as same as experiment example 2 except that stimulation tone was given at 8 kHz tone burst (TB) from 70 dB and decreased by 5 dB. The obtained result is shown at FIG. 6.

Figure 6:
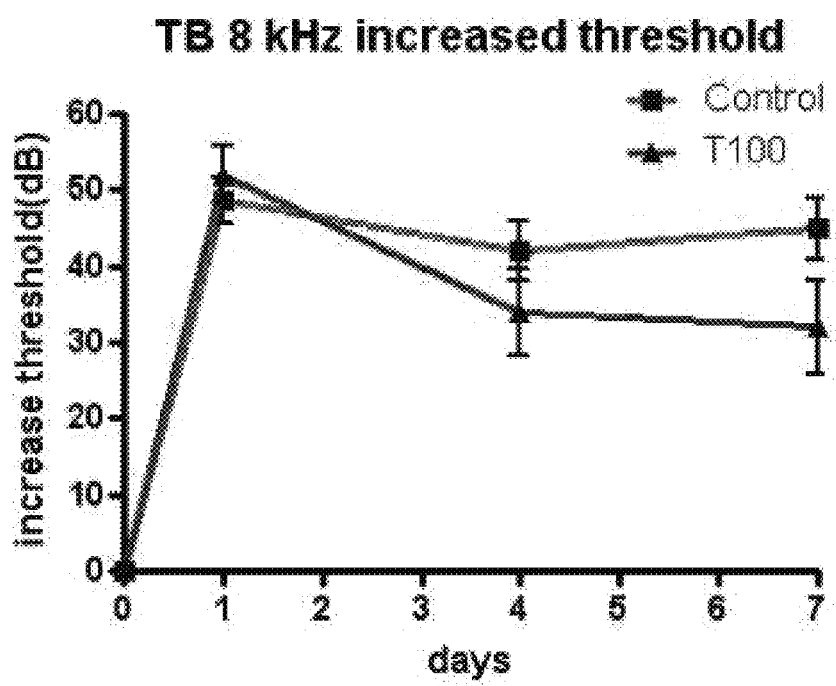
FIG. 6 shows the measurement of *Cuscuta japonica Choisy* extract in hearing threshold test by auditory brainstem response (ABR) with 8 kHz TB stimulation tone after exposure to noise (control: not treated group, T100: test group treated with *Cuscuta japonica Choisy* extract).

As shown in FIG. 6, control group showed increased hearing threshold at 24 hours after exposure to noise and maintained similar threshold for 7 days which suggesting permanent hearing damage. Meanwhile, *Cuscuta japonica Choisy* extract (T100) treated group showed the decrease in threshold since 4 days after exposure to noise, and 20 dB decrease than before administration shown at 7 days after exposure identified ameliorating effects compared to control group. As found in test results with click stimulation tone and 3, 4 and 6 kHz TB stimulation tone, ameliorating effects on hearing threshold with *Cuscuta japonica Choisy* extract (T100) treated group was found to identify that *Cuscuta japonica Choisy* extract (T100) is effective in preventing and treating noise-induced hearing loss.

Experiment Example 7

Identification of Protective Effect on Hair Cells with the Extract of *Rehmannia glutinosa Libschitz* Var. *Purpurea MAKINO* and *Cuscuta japonica Choisy* after Exposure to Noise-Transient Evoked Otoacoustic Emission (TEOAE) Experiment In order to compare the effect of steamed *Rehmannia glutinosa Libschitz* var. *purpurea MAKINO* extract, and the extract of *Rehmannia glutinosa Libschitz* var. *purpurea MAKINO* and *Cuscuta japonica Choisy* on hair cells of cochlea after exposure to noise, transient evoked otoacoustic emission (TEOAE) experiment was conducted.

Experiment was conducted as same as experiment example 1 except that 3 groups, each comprising 8 mice test group to be treated with 100 mg/kg of the extract of *Rehmannia glutinosa Libschitz* var. *purpurea MAKINO* and *Cuscuta japonica Choisy* prepared from example 2, 8 mice test group to be treated with 100 mg/kg of steamed *Rehmannia glutinosa Libschitz* var. *purpurea MAKINO* extract prepared from comparative example 1 and 8 mice of control group not to be treated were tested. The obtained result is shown in FIG. 7.

Figure 7:
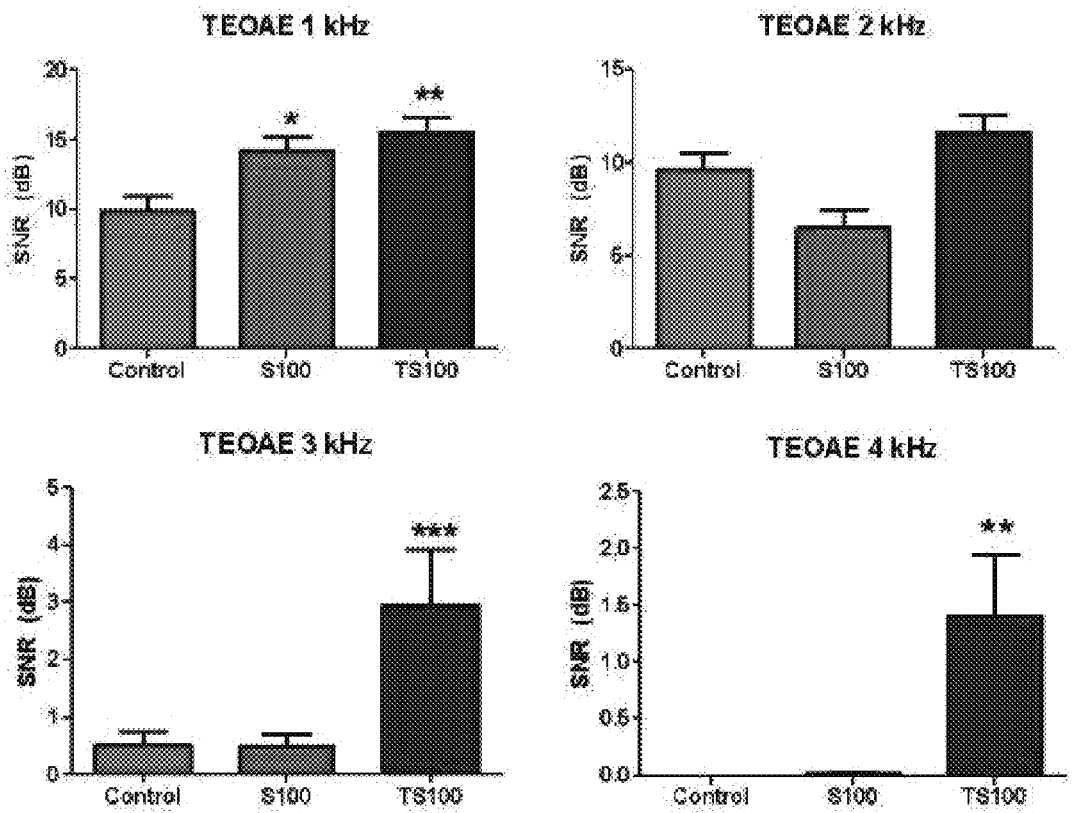
FIG. 7 shows the measurement of the extract of *Rehmannia glutinosa Libschitz* var. *purpurea MAKINO* and *Cuscuta japonica Choisy* in transient evoked otoacoustic emission (TEOAE) test after exposure to noise (control: not treated group, S100: comparative test group treated with steamed *Rehmannia glutinosa Libschitz* var. *purpurea MAKINO* extract, TS100: test group treated with the extract of *Rehmannia glutinosa Libschitz* var. *purpurea MAKINO* and *Cuscuta japonica Choisy*).

As shown in FIG. 7, at 1 kHz TEOAE, both steamed *Rehmannia glutinosa Libschitz* var. *purpurea MAKINO* extract (S100) treated group and the group treated with the extract of *Rehmannia glutinosa Libschitz* var. *purpurea MAKINO* and *Cuscuta japonica Choisy* (TS100) showed significant higher TEOAE response than control group, while at 2 kHz, the test group treated with the extract of *Rehmannia glutinosa Libschitz* var. *purpurea MAKINO* and *Cuscuta japonica Choisy* (TS100) showed highest TEOAE response but without significant difference. At 3 kHz TEOAE, the test group treated with the extract of *Rehmannia glutinosa Libschitz* var. *purpurea MAKINO* and *Cuscuta japonica Choisy* (TS100) showed significant higher TEOAE response, and at 4 kHz TEOAE, only the test group treated with the extract of *Rehmannia glutinosa Libschitz* var. *purpurea MAKINO* and *Cuscuta japonica Choisy* (TS100) showed significant high TEOAE response. Control group showed clear damage on hair cells demonstrated by low level of response at 3 and 4 kHz TEOAE particularly, while the test group treated with the extract of *Rehmannia glutinosa Libschitz* var. *purpurea MAKINO* and *Cuscuta japonica Choisy* (TS100) showed less damage on hair cells at both frequencies after exposure to noise.

Experiment Example 8

Identification of Ameliorating Effect on Hearing with the Extract of *Rehmannia glutinosa Libschitz* Var. *Purpurea MAKINO* and *Cuscuta japonica Choisy* after Exposure to Noise—By Using Click Stimulation Tone In order to compare the effect of steamed *Rehmannia glutinosa Libschitz* var. *purpurea MAKINO* extract, and the extract of *Rehmannia glutinosa Libschitz* var. *purpurea MAKINO* and *Cuscuta japonica* with regard to the presence of hearing sense by measuring threshold after exposure to noise, hearing threshold experiment was conducted by using auditory brainstem response (ABR).

Experiment was conducted as same as experiment example 2 except that 3 groups, each comprising 8 mice test group to be treated with 100 mg/kg of the extract of *Rehmannia glutinosa Libschitz* var. *purpurea MAKINO* and *Cuscuta japonica Choisy* prepared from example 2, 8 mice test group to be treated with 100 mg/kg of steamed *Rehmannia glutinosa Libschitz* var. *purpurea MAKINO* extract prepared from comparative example 1 and 8 mice of control group not to be treated were tested. The obtained result is shown in FIG. 8.

Figure 8:
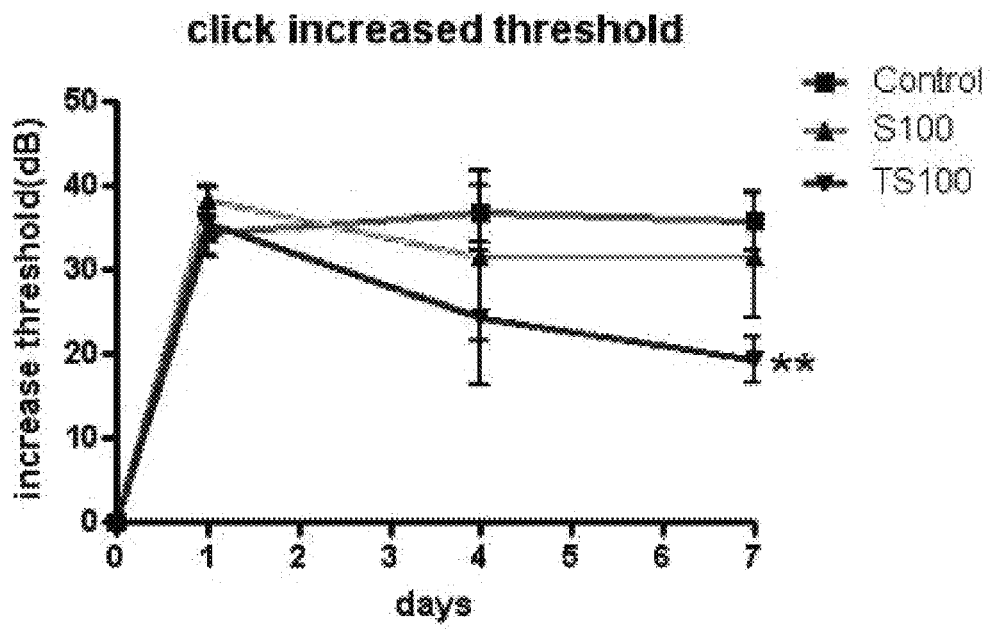
FIG. 8 shows the measurement of the extract of *Rehmannia glutinosa Libschitz* var. *purpurea MAKINO* and *Cuscuta japonica Choisy* in hearing threshold test by auditory brainstem response (ABR) with click stimulation tone after exposure to noise (control: not treated group, S100: comparative test group treated with steamed *Rehmannia glutinosa Libschitz* var. *purpurea MAKINO* extract, TS100: test group treated with the extract of *Rehmannia glutinosa Libschitz* var. *purpurea MAKINO* and *Cuscuta japonica Choisy*).

As shown in FIG. 8, all three groups showed similar threshold increase when measured at 24 hours after exposure to noise, and control group maintained similar increase in hearing threshold for 7 days suggesting permanent hearing damage. Steamed *Rehmannia glutinosa Libschitz* var. *purpurea MAKINO* extract (S100) treated group showed slight decrease in threshold since 4 days after exposure to noise but no significant difference with control group was shown. Meanwhile, the test group treated with the extract of *Rehmannia glutinosa Libschitz* var. *purpurea MAKINO* and *Cuscuta japonica* (TS100) treated group showed considerable decrease in threshold since 4 days after exposure to noise and 20 dB decrease than before administration shown at 7 days after exposure identified significant ameliorating effects compared to control group. Since the test group treated with the extract of *Rehmannia glutinosa Libschitz* var. *purpurea MAKINO* and *Cuscuta japonica* (TS100) showed higher ameliorating effect on hearing threshold than the group treated with Steamed *Rehmannia glutinosa Libschitz* var. *purpurea MAKINO* extract (S100), preventive and therapeutic effects of the extract of *Rehmannia glutinosa Libschitz* var. *purpurea MAKINO* and *Cuscuta japonica Choisy* (TS100) on noise-induced hearing loss was identified.

Experiment Example 9

Identification of Ameliorating Effect on Hearing with the Extract of *Rehmannia glutinosa Libschitz* Var. *Purpurea MAKINO* and *Cuscuta japonica Choisy* after Exposure to Noise—By Using 3 kHz TB Stimulation Tone In order to compare the ameliorating effect on hearing of steamed *Rehmannia glutinosa Libschitz* var. *purpurea MAKINO* extract, and the extract of *Rehmannia glutinosa Libschitz* var. *purpurea MAKINO* and *Cuscuta japonica* by measuring hearing threshold at 3 kHz stimulation tone after exposure to noise, hearing threshold was measured by using auditory brainstem response (ABR).

Experiment was conducted as same as experiment example 8 except that stimulation tone at the time of ABR test was given at 3 kHz tone burst (TB) from 70 dB and decreased by 5 dB. The obtained result is shown at FIG. 9.

Figure 9:
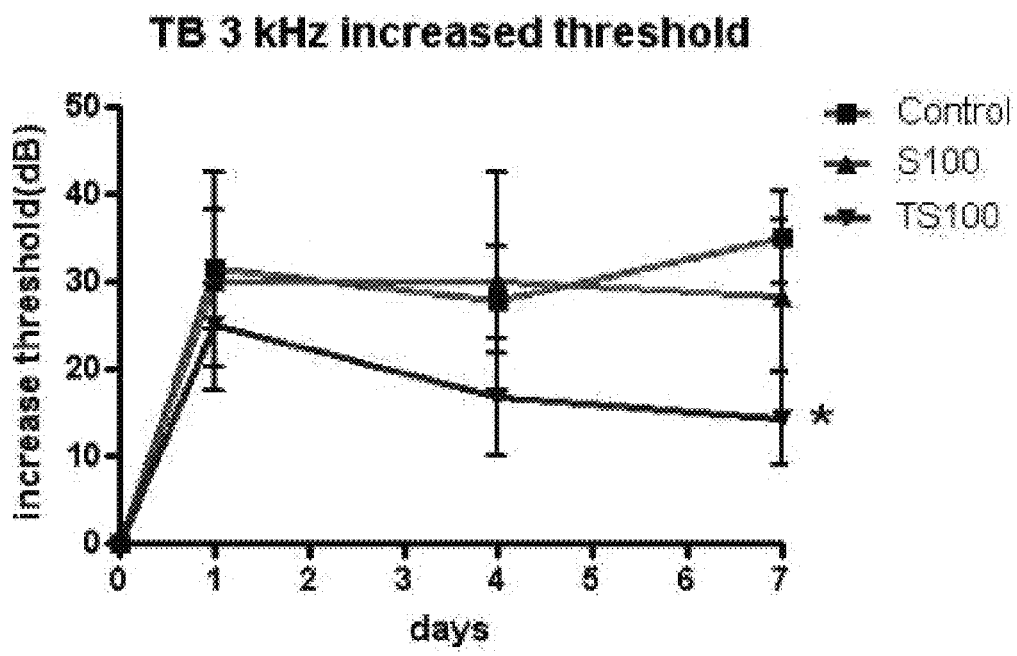
FIG. 9 shows the measurement of the extract of *Rehmannia glutinosa Libschitz* var. *purpurea MAKINO* and *Cuscuta japonica Choisy* in hearing threshold test by auditory brainstem response (ABR) with 3 kHz TB stimulation tone after exposure to noise (control: not treated group, S100: comparative test group treated with steamed *Rehmannia glutinosa Libschitz* var. *purpurea MAKINO* extract, TS100: test group treated with the extract of *Rehmannia glutinosa Libschitz* var. *purpurea MAKINO* and *Cuscuta japonica Choisy*).

As shown in FIG. 9, all three group showed 25-30 dB of threshold increase measured after exposure to noise, and control group showed similar or increased hearing threshold for 7 days suggesting permanent hearing damage. Steamed *Rehmannia glutinosa Libschitz* var. *purpurea MAKINO* extract (S100) treated group showed similar level of hearing threshold with control group without showing improvement effect on hearing. Meanwhile, the test group treated with the extract of *Rehmannia glutinosa Libschitz* var. *purpurea MAKINO* and *Cuscuta japonica* (TS100) showed considerable decrease in threshold since 4 days after exposure to noise and 10 dB decrease than before administration shown at 7 days after exposure identified significant ameliorating effects compared to control group. As with the test result with click stimulation tone, the test group treated with the extract of *Rehmannia glutinosa Libschitz* var. *purpurea MAKINO* and *Cuscuta japonica* (TS100) showed higher ameliorating effect on hearing threshold than the group treated with Steamed *Rehmannia glutinosa Libschitz* var. *purpurea MAKINO* extract (S100), thereby preventive and therapeutic effects of the extract of *Rehmannia glutinosa Libschitz* var. *purpurea MAKINO* and *Cuscuta japonica Choisy* (TS100) on noise-induced hearing loss was identified.

Experiment Example 10

Identification of Ameliorating Effect on Hearing with the Extract of *Rehmannia glutinosa Libschitz* Var. *Purpurea MAKINO* and *Cuscuta japonica Choisy* after Exposure to Noise—By Using 4 kHz TB Stimulation Tone In order to compare the ameliorating effect on hearing of steamed *Rehmannia glutinosa Libschitz* var. *purpurea*

MAKINO extract, and the extract of *Rehmannia glutinosa Libschitz* var. *purpurea MAKINO* and *Cuscuta japonica* by measuring hearing threshold at 4 kHz stimulation tone after exposure to noise, hearing threshold was measured by using auditory brainstem response (ABR).

Experiment was conducted as same as experiment example 8 except that stimulation tone at the time of ABR test was given at 4 kHz tone burst (TB) from 70 dB and decreased by 5 dB. The obtained result is shown at FIG. 10.

Figure 10:
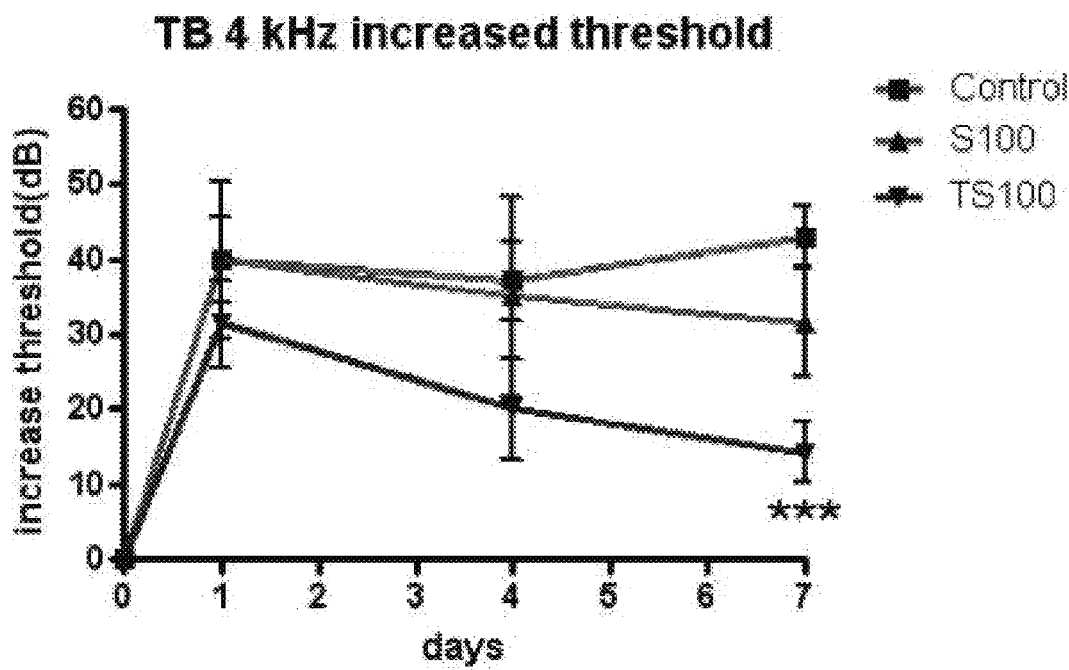
FIG. 10 shows the measurement of the extract of *Rehmannia glutinosa Libschitz* var. *purpurea MAKINO* and *Cuscuta japonica Choisy* in hearing threshold test by auditory brainstem response (ABR) with 4 kHz TB stimulation tone after exposure to noise (control: not treated group, S100: comparative test group treated with steamed *Rehmannia glutinosa Libschitz* var. *purpurea MAKINO* extract, TS100: test group treated with the extract of *Rehmannia glutinosa Libschitz* var. *purpurea MAKINO* and *Cuscuta japonica Choisy*).

As shown in FIG. 10, all three group showed 30-40 dB of threshold increase when measured after exposure to noise, and control group showed similar or increased hearing threshold for 7 days suggesting permanent hearing damage. Steamed *Rehmannia glutinosa Libschitz* var. *purpurea MAKINO* extract (S100) treated group showed 9 dB decrease in hearing threshold at 7 days after exposure to noise but showed no significant difference with control group. Meanwhile, the test group treated with the extract of *Rehmannia glutinosa Libschitz* var. *purpurea MAKINO* and *Cuscuta japonica* (TS100) showed considerable decrease in threshold since 4 days after exposure to noise and 17 dB decrease than before administration shown at 7 days after exposure identified significant ameliorating effects compared to control group. As with the test results with click stimulation tone and 3 kHz TB stimulation tone, the test group treated with the extract of *Rehmannia glutinosa Libschitz* var. *purpurea MAKINO* and *Cuscuta japonica* (TS100) showed higher ameliorating effect on hearing threshold than the group treated with Steamed *Rehmannia glutinosa Libschitz* var. *purpurea MAKINO* extract (S100), thereby preventive and therapeutic effects of the extract of *Rehmannia glutinosa Libschitz* var. *purpurea MAKINO* and *Cuscuta japonica Choisy* (TS100) on noise-induced hearing loss was identified.

Experiment Example 11

Identification of Ameliorating Effect on Hearing with the Extract of *Rehmannia glutinosa Libschitz* Var. *Purpurea MAKINO* and *Cuscuta japonica Choisy* after Exposure to Noise—By Using 6 kHz TB Stimulation Tone In order to compare the ameliorating effect on hearing of steamed *Rehmannia glutinosa Libschitz* var. *purpurea MAKINO* extract, and the extract of *Rehmannia glutinosa Libschitz* var. *purpurea MAKINO* and *Cuscuta japonica* by measuring hearing threshold at 6 kHz stimulation tone after exposure to noise, hearing threshold was measured by using auditory brainstem response (ABR).

Experiment was conducted as same as experiment example 8 except that stimulation tone at the time of ABR test was given at 6 kHz tone burst (TB) which frequency is close to the stimulation tone used in noise exposure from 70 dB and decreased by 5 dB. The obtained result is shown at FIG. 11.

Figure 11:
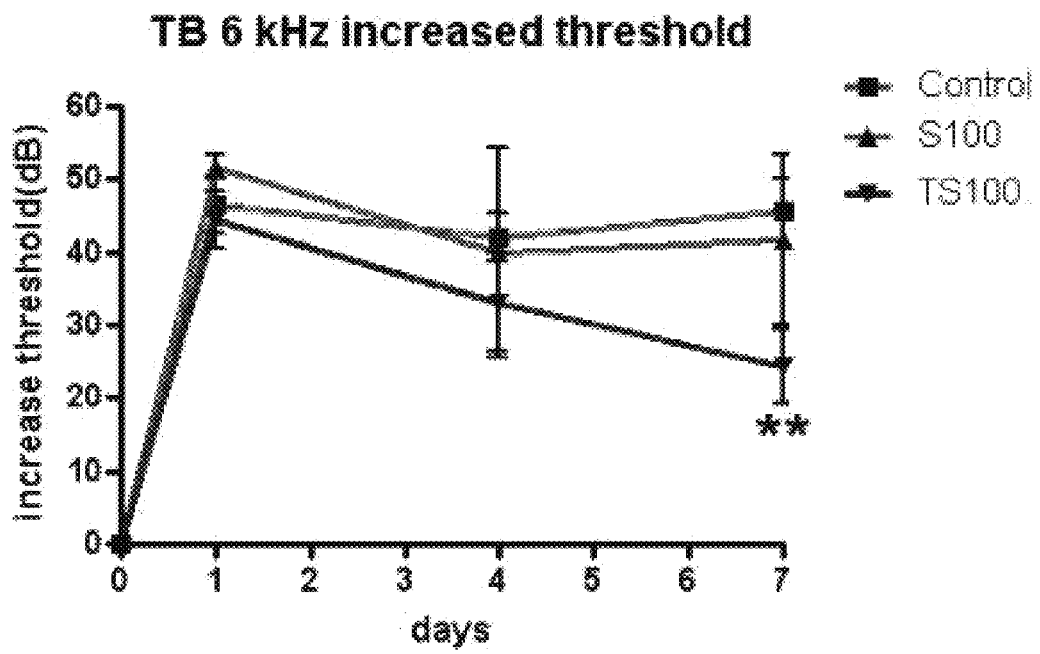
FIG. 11 shows the measurement of the extract of *Rehmannia glutinosa Libschitz* var. *purpurea MAKINO* and *Cuscuta japonica Choisy* in hearing threshold test by auditory brainstem response (ABR) with 6 kHz TB stimulation tone after exposure to noise (control: not treated group, S100: comparative test group treated with steamed *Rehmannia glutinosa Libschitz* var. *purpurea MAKINO* extract, TS100: test group treated with the extract of *Rehmannia glutinosa Libschitz* var. *purpurea MAKINO* and *Cuscuta japonica Choisy*).

As shown in FIG. 11, all three group showed 43-51 dB of threshold increase when measured after exposure to noise, and control group showed similar or increased hearing threshold for 7 days suggesting permanent hearing damage. Steamed *Rehmannia glutinosa Libschitz* var. *purpurea MAKINO* extract (S100) treated group showed 10 dB decrease in hearing threshold at 7 days after exposure to noise but showed no significant difference with control group. Meanwhile, the test group treated with the extract of *Rehmannia glutinosa Libschitz* var. *purpurea MAKINO* and *Cuscuta japonica* (TS100) showed considerable decrease in threshold since 4 days after exposure to noise and 21 dB decrease than before administration shown at 7 days after exposure identified significant ameliorating effects compared to control group. As with the test results with click stimulation tone and 3 kHz and 4 kHz TB stimulation tone, the test group treated with the extract of *Rehmannia glutinosa Libschitz* var. *purpurea MAKINO* and *Cuscuta japonica* (TS100) showed higher ameliorating effect on hearing threshold than the group treated with Steamed *Rehmannia glutinosa Libschitz* var. *purpurea MAKINO* extract (S100), thereby preventive and therapeutic effects of the extract of *Rehmannia glutinosa Libschitz* var. *purpurea MAKINO* and *Cuscuta japonica Choisy* (TS100) on noise-induced hearing loss was identified.

Experiment Example 12

Identification of Ameliorating Effect on Hearing with the Extract of *Rehmannia glutinosa Libschitz* Var. *Purpurea MAKINO* and *Cuscuta japonica Choisy* after Exposure to Noise—By Using 8 kHz TB Stimulation Tone In order to compare the ameliorating effect on hearing of steamed *Rehmannia glutinosa Libschitz* var. *purpurea MAKINO* extract, and the extract of *Rehmannia glutinosa Libschitz* var. *purpurea MAKINO* and *Cuscuta japonica* by measuring hearing threshold at 8 kHz stimulation tone after exposure to noise, hearing threshold was measured by using auditory brainstem response (ABR).

Experiment was conducted as same as experiment example 8 except that stimulation tone at the time of ABR test was given at 8 kHz tone burst (TB) from 70 dB and decreased by 5 dB. The obtained result is shown at FIG. 12.

Figure 12:
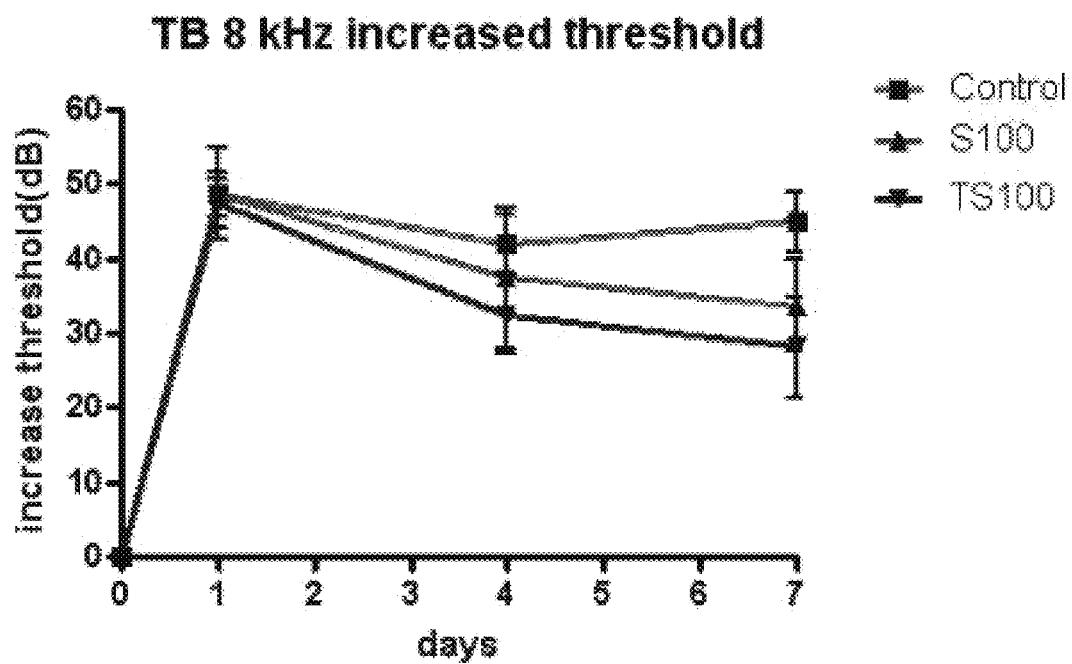
FIG. 12 shows the measurement of the extract of *Rehmannia glutinosa Libschitz* var. *purpurea MAKINO* and *Cuscuta japonica Choisy* in hearing threshold test by auditory brainstem response (ABR) with 8 kHz TB stimulation tone after exposure to noise (control: not treated group, S100: comparative test group treated with steamed *Rehmannia glutinosa Libschitz* var. *purpurea MAKINO* extract, TS100: test group treated with the extract of *Rehmannia glutinosa Libschitz* var. *purpurea MAKINO* and *Cuscuta japonica Choisy*).

As shown in FIG. 12, all three group showed 41-50 dB of threshold increase when measured after exposure to noise, and control group showed similar or increased hearing threshold for 7 days suggesting permanent hearing damage. Steamed *Rehmannia glutinosa Libschitz* var. *purpurea MAKINO* extract (S100) treated group showed 17 dB decrease in hearing threshold at 7 days after exposure to noise but showed no significant difference with control group. Meanwhile, the test group treated with the extract of *Rehmannia glutinosa Libschitz* var. *purpurea MAKINO* and *Cuscuta japonica* (TS100) showed considerable decrease in threshold since 4 days after exposure to noise and 23 dB decrease than before administration shown at 7 days after exposure identified significant ameliorating effects compared to control group. As with the test results with click stimulation tone and 3, 4 and 6 kHz TB stimulation tone, the test group treated with the extract of *Rehmannia glutinosa Libschitz* var. *purpurea MAKINO* and *Cuscuta japonica* (TS100) showed higher ameliorating effect on hearing threshold than the group treated with Steamed *Rehmannia glutinosa Libschitz* var. *purpurea MAKINO* extract (S100), thereby preventive and therapeutic effects of the extract of *Rehmannia glutinosa Libschitz* var. *purpurea MAKINO* and *Cuscuta japonica Choisy* (TS100) on noise-induced hearing loss was identified.

As described above, *Cuscuta japonica Choisy* extract, and the extract of *Rehmannia glutinosa Libschitz* var. *purpurea MAKINO* and *Cuscuta japonica Choisy* are useful to prevent and treat hearing loss such as noise-induced hearing loss by protecting hair cells from damage and decreasing hearing threshold measured from auditory nerve. Therefore, *Cuscuta japonica Choisy* extract, and the extract of *Rehmannia*

*glutinosa Libschitz* var. *purpurea MAKINO* and *Cuscuta japonica Choisy* can be used for preventing and treating sensorineural hearing loss.

Preparation Examples

By using the extract of *Rehmannia glutinosa Libschitz* var. *purpurea MAKINO* and *Cuscuta japonica Choisy* prepared from Example 2, following formulations were prepared. However, following preparation examples are only to illustrate the present invention, not to restrict the content of the invention thereto.

Preparation Example 1. Preparation of Tablets

| | |
|---|---|
| The extract of *Rehmannia glutinosa* Libschitz var. purpurea MAKINO and *Cuscuta japonica* Choisy | 200 mg |
| Lactose | 100 mg |
| Starch | 100 mg |
| Magnesium stearate | q.s. |

The above ingredients were mixed and compacted according to conventional methods to prepare tablets.

Preparation Example 2. Preparation of Solutions

| | |
|---|---|
| The extract of *Rehmannia glutinosa* Libschitz var. purpurea MAKINO and *Cuscuta japonica* Choisy | 1000 mg |
| CMC-Na | 20 g |
| Isomerose | 20 g |
| Lemon fragrance | q.s. |

Purified water was added to make 1000 ml. The above ingredients were mixed and filled into amber bottles according to conventional methods to prepare solution.

Preparation Example 3. Preparation of Capsules

| | |
|---|---|
| The extract of *Rehmannia glutinosa* Libschitz var. purpurea MAKINO and *Cuscuta japonica* Choisy | 300 mg |
| Crystalline cellulose | 3 mg |
| Lactose | 14.8 mg |
| Magnesium stearate | 0.2 mg |

The above ingredients were mixed and filled into gelatin capsules according to conventional methods to prepare capsules.

Preparation Example 4. Preparation of Injections

| | |
|---|---|
| The extract of *Rehmannia glutinosa* Libschitz var. purpurea MAKINO and *Cuscuta japonica* Choisy | 300 mg |
| Mannitol | 180 mg |
| Sterilized distilled water for injection | 2974 mg |
| $Na_2HPO_4 12H_2O$ | 26 mg |

It was prepared with the above amount of ingredients per ample (2) according to conventional methods for preparing injections.

The invention claimed is:

1. A method for treating hearing loss, comprising administering an effective amount of a composition comprising an extract containing a combination of *Rehmannia glutinosa Libschitz* var. *purpurea MAKINO* and *Cuscuta japonica Choisy*, to a subject in need thereof,
wherein the extract contains the *Rehmannia glutinosa Libschitz* var. *purpurea MAKINO* and the *Cuscuta japonica Choisy* in a weight ratio of 1:1.8 to 1:9.

2. The method according to claim 1, wherein the hearing loss is noise-induced hearing loss.

3. The method according to claim 2, wherein the *Rehmannia glutinosa Libschitz* var. *purpurea MAKINO* is at least one selected from the group consisting of raw *Rehmannia glutinosa Libschitz* var. *purpurea MAKINO*, dried *Rehmannia glutinosa Libschitz* var. *purpurea MAKINO* and steamed *Rehmannia glutinosa Libschitz* var. *purpurea MAKINO*.

4. The method according to claim 1, wherein the extract of *Rehmannia glutinosa Libschitz* var. *purpurea MAKINO* and the extract of *Cuscuta japonica Choisy* are obtained by extracting the *Rehmannia glutinosa Libschitz* var. *purpurea MAKINO* and the *Cuscuta japonica Choisy* plant, individually or together, with an extraction solvent selected from the group consisting of water, a $C_1$-$C_4$ alcohol, and a mixed solvent of water and a $C_1$-$C_4$ alcohol.

5. The method according to claim 4, wherein the *Rehmannia glutinosa Libschitz* var. *purpurea MAKINO* is at least one selected from the group consisting of raw *Rehmannia glutinosa Libschitz* var. *purpurea MAKINO*, dried *Rehmannia glutinosa Libschitz* var. *purpurea MAKINO* and steamed *Rehmannia glutinosa Libschitz* var. *purpurea MAKINO*.

6. The method according to claim 1, wherein the *Rehmannia glutinosa Libschitz* var. *purpurea MAKINO* is at least one selected from the group consisting of raw *Rehmannia glutinosa Libschitz* var. *purpurea MAKINO*, dried *Rehmannia glutinosa Libschitz* var. *purpurea MAKINO* and steamed *Rehmannia glutinosa Libschitz* var. *purpurea MAKINO*.

7. A method for ameliorating hearing loss, comprising administering an effective amount of a composition comprising an extract containing a combination of *Rehmannia glutinosa Libschitz* var. *purpurea MAKINO* and *Cuscuta japonica Choisy*, to a subject in need thereof,
wherein the extract contains the *Rehmannia glutinosa Libschitz* var. *purpurea MAKINO* and the *Cuscuta japonica Choisy* in a weight ratio of 1:1.8 to 1:9.

8. The method according to claim 7, wherein the *Rehmannia glutinosa Libschitz* var. *purpurea MAKINO* is at least one selected from the group consisting of raw *Rehmannia glutinosa Libschitz* var. *purpurea MAKINO*, dried *Rehmannia glutinosa Libschitz* var. *purpurea MAKINO* and steamed *Rehmannia glutinosa Libschitz* var. *purpurea MAKINO*.

9. The method according to claim 7, wherein the hearing loss is noise-induced hearing loss.

10. The method according to claim 9, wherein the *Rehmannia glutinosa Libschitz* var. *purpurea MAKINO* is at least one selected from the group consisting of raw *Rehmannia glutinosa Libschitz* var. *purpurea MAKINO*, dried *Rehmannia glutinosa Libschitz* var. *purpurea MAKINO* and steamed *Rehmannia glutinosa Libschitz* var. *purpurea MAKINO*.

11. The method according to claim 7, wherein the extract of *Rehmannia glutinosa Libschitz* var. *purpurea MAKINO* and the extract of *Cuscuta japonica Choisy* are obtained by extracting the *Rehmannia glutinosa Libschitz* var. *purpurea MAKINO* and the *Cuscuta japonica Choisy* plant, individually or together, with an extraction solvent selected from the group consisting of water, a $C_1$-$C_4$ alcohol, and a mixed solvent of water and a $C_1$-$C_4$ alcohol.

12. The method according to claim 11, wherein the *Rehmannia glutinosa Libschitz* var. *purpurea MAKINO* is at least one selected from the group consisting of raw *Rehmannia glutinosa Libschitz* var. *purpurea MAKINO*, dried *Rehmannia glutinosa Libschitz* var. *purpurea MAKINO* and steamed *Rehmannia glutinosa Libschitz* var. *purpurea MAKINO*.

13. A method for treating or ameliorating hearing loss, consisting of administering an effective amount of a composition comprising an extract containing a combination of *Rehmannia glutinosa Libschitz* var. *purpurea MAKINO* and *Cuscuta japonica Choisy*, to a subject in need thereof,
    wherein the extract contains the *Rehmannia glutinosa Libschitz* var. *purpurea MAKINO* and the *Cuscuta japonica Choisy* in a weight ratio of 1:1.8 to 1:9.

* * * * *